United States Patent [19]
Diaz et al.

[11] Patent Number: 6,048,532
[45] Date of Patent: *Apr. 11, 2000

[54] CHEMICAL COMPOSITION AND METHOD FOR AIDING THE ABSORPTION, BINDING AND ELIMINATION OF UNDIGESTED FAT AND REDUCING CHOLESTEROL IN THE HUMAN BODY

[76] Inventors: Jose A. Diaz, 2950 Jackson Ave., Coconut Grove, Fla. 33133; Eduardo M. Naranjo, 14021 Cypress Ct., Miami Lakes, Fla. 33014

[ * ] Notice: This patent is subject to a terminal disclaimer.

[21] Appl. No.: 09/135,920

[22] Filed: Aug. 18, 1998

Related U.S. Application Data

[63] Continuation-in-part of application No. 08/888,848, Jul. 7, 1997, Pat. No. 5,795,576
[60] Provisional application No. 60/021,299, Jul. 8, 1996.
[51] Int. Cl.[7] .......................... A61K 35/78; A61K 31/702
[52] U.S. Cl. ............................. 424/195.1; 514/54; 514/62
[58] Field of Search ........................... 424/195.1; 514/54, 514/62

[56] References Cited

U.S. PATENT DOCUMENTS

| | | |
|---|---|---|
| 3,533,940 | 10/1970 | Peniston et al. . |
| 3,879,376 | 4/1975 | Vanlerberghe et al. . |
| 3,953,608 | 4/1976 | Vanlerberghe et al. . |
| 4,034,121 | 7/1977 | Dunn et al. . |
| 4,119,619 | 10/1978 | Rogozhin et al. . |
| 4,223,023 | 9/1980 | Furda . |
| 5,795,576 | 8/1998 | Diaz et al. ........................ 424/195.1 |

*Primary Examiner*—Raymond Henley, III
*Attorney, Agent, or Firm*—Malloy & Malloy, P.A.

[57] ABSTRACT

A composition and method for reducing cholesterol is provided for ingestion by humans to aid in absorbing and bind undigested fat for rapid elimination from the human body. This composition, in a preferred embodiment comprises at least one fibrous agent, such as psyllium, in an amount of generally about 85% by weight of the composition, an amount of glucosamine and preferably glucosamine HCL at generally about 6% by weight of the composition, and amounts of glucomannan, apple pectin, and stearic acid forming the other generally about 10% by weight of the composition.

20 Claims, No Drawings

CHEMICAL COMPOSITION AND METHOD FOR AIDING THE ABSORPTION, BINDING AND ELIMINATION OF UNDIGESTED FAT AND REDUCING CHOLESTEROL IN THE HUMAN BODY

CLAIM OF PRIORITY

The present application is a continuation-in-part patent application of patent application Ser. No. 08/888,848, filed on Jul. 7, 1997, now U.S. Pat. No. 5,795,570, which claims priority under 35 U.S.C. Section 119(e) to a provisional patent application filed with the U.S. Patent Office on Jul. 8, 1996 and assigned Ser. No. 60/021,299, both of which are incorporated herein by reference.

BACKGROUND OF THE INVENTION

1. Field of the Invention

The present invention relates to a chemical composition and a method of reducing cholesterol as well as accomplishing weight loss in humans whereby a human ingests the chemical composition in recommended dosages prior to eating a meal, and thereby, facilitates the absorption and binding of undigested fat to a fibrous agent for rapid elimination from the human body.

2. Description of the Related Art

In this day and age, many people's lifestyles have become less physically active. A natural result of a sedentary lifestyle is the tendency to gain weight, which is further compounded by the modern day tendency of many people to consume food which has a high fat content. Indeed, it is commonly thought that many people are now over-weight or at least moderately obese, and such individuals typically suffer from certain health problems associated with such conditions, at least at some later point in life, if not sooner than expected. Due to this trend, countless efforts have been made to help people control their weight. As a few examples, many have proclaimed to have won the "battle of the bulge" with a specific diet program or a particular exercise program. Others in the scientific arena have formulated sugar substitutes and are pursuing fat substitutes as methods to reduce the caloric intake of an individual, which hopefully do not sacrifice the taste of appealing but highly fattening foods. While these efforts are generally capable of aiding many in their fight to lose weight and establish a healthier life style, many such attempts are generally ineffective or simply not practical. For example, some good meaning souls have tried in earnest to follow a particular diet plan but eventually, deviate from the plan because of lack of will-power to continue a given program for weeks or months at a time. Finally, some view sugar substitutes as being tasteless or carrying an intolerable health risk, given that some studies have linked them to carcinogens and/or the formation of brain tumors.

It has been appreciated in recent years that the fat content of foods which people eat are a major culprit behind weight gain. For example, regardless of the type of fat present in a food product, fat has the highest caloric value per gram—about 9 calories per gram—of any food group. It is understood that the body tends to store fat for future use, rather than to utilize it immediately, and this factor helps lead to weight-gain. However, it has also been appreciated in recent years that there is a connection between the amount of fat stored in the body and the level of cholesterol in the body, with a diet high in fat likely to lead to high cholesterol levels. As cholesterol has been implicated as a factor in arteriosclerosis or hardening of the arteries, the risk for heart disease and/or a heart attack is elevated when a diet high in fat is followed. Unfortunately, fat also makes many food items more tasty—whether butter on bread, dressings on salads, sour cream on potatoes, or frosting on cake—and are therefore, difficult to eliminate entirely from one's diet. Thus, fat usually finds its way into the body. Once it does so, a healthy body automatically proceeds with the digestion process by the secretion of lipase, an enzyme that accelerates synthesis of fats, i.e., breaking down the fat molecule. The majority of all fats in foods are present in "triglyceride form", which the body seeks to break down by removing the glycerol molecule from the triglyceride and thereby, release the free fatty acids. Once this occurs, the body is well on its way to absorbing and storing the fat instead of utilizing it for energy.

From the foregoing, it will be understood that there remains an appreciable need in the art for a product and attendant safe and easy method of treatment which facilitates a person's efforts to lose weight and to control the accumulation of harmful cholesterol. Any such product and method should be capable of aiding a person in accomplishing these goals, without relying exclusively on a person's having sufficient will-power to maintain a strict diet and/or a rigorous exercise program. In addition, any such product and method should not interfere with the taste of foods. Ideally, any such product or method would permit a person to eat the foods that they most like, while not being as mindful about the amount of fats contained therein and would prevent the body from absorbing the fat in such foods once they have been eaten. Any such product and method would also ideally aid the body in rapid elimination of the ingested fats in a safe, comfortable and natural manner. In turn, the rapid elimination of fats subsequent to ingestion and prior to digestion would have a highly beneficial effect in preventing the build-up or accumulation of harmful cholesterol. The present invention is designed to satisfy the needs in the art and is believed to represent a significant advance in improving a person's health by the reduction of harmful cholesterol, while facilitating weight loss by means of the rapid elimination of fat from the human body.

SUMMARY OF THE INVENTION

The present invention is directed to a novel chemical composition intended for ingestion by humans and a method which aids in reducing cholesterol as well as with weight loss. In particular, when the chemical composition of the present invention is ingested by a human prior to eating a meal, the composition acts to absorb and bind undigested fat to a fibrous agent so as to promote its rapid and natural elimination from the human body. In accordance with this invention, the novel composition is preferably moisture activated such that it remains inert and can be formed into capsules, and preferably ones that are conveniently sized into predetermined doses for ingestion by a human, and that will remain inert until coming into contact with bodily secretions, whether water of other liquid.

The chemical composition of the present invention preferably comprises a mixture of an amount of at least one fibrous agent, such as psyllium, at generally about 85% by weight, an amount of glucosamine HCL at generally about 6% or 7% by weight, an amount of glucomannan at generally about 5% and 6% by weight, an amount of fruit or vegetable derived pectin such as apple pectin generally about 2% by weight, and an amount of stearic acid generally between 1% and 2% by weight of the composition. Upon contact with moisture, the preferred composition begins to break down and becomes activated. Once activated, the composition acts quickly, usually within 30 seconds to seek and attach itself to undigested fats such as but not limited to oils and the like, and typically, within about 2 minutes will form a small mass of undigestible fibrous material. Additionally, a method for using the chemical composition is also described which comprises the steps of forming a single dose capsule of preferably about seven hundred milligrams (700 mgs) which contains the chemical composition, and having a human ingest at least four of such capsules, preferably with about eight ounces of water between fifteen and twenty minutes prior to a meal. While the size of the individual single dose capsule may vary, the preferred method of the present invention includes having a human ingest substantially about twenty-eight hundred milligrams (2800 mgs) of the composition before each meal. The method of this invention is believed to offer compelling results in reducing the cholesterol levels of a human following the steps of the method, which results would only be enhanced if a diet low in fatty foods and a regiment of regular exercise were also followed.

A primary object of the present invention is to provide a chemical composition and method of treatment which serve as convenient and effective means for reducing the quantity of fat digested and/or absorbed by the human body, thereby aiding in a significant reduction of harmful cholesterol and the build-up or collection of cholesterol deposits in the cardiovascular system.

Another primary object of the present invention is to provide a chemical composition and method of treatment which seeks out, attaches and binds undigested fat, ingested by a human, to a fibrous agent, forming an undigestible mass which can easily and rapidly be eliminated from the human's body.

A feature of the chemical composition according to the present invention is that it is moisture activated and therefore is inert and can be formed into and stored as conveniently sized capsules until being ingested by a human and activated by coming in contact with bodily secretions whether water or other liquid.

Yet another object of the present invention is to provide a chemical composition which includes a blend of fibrous material for aiding the human body in rapid elimination of waste.

A feature of the present invention is that it can absorb up to twelve times its own weight of undigested fats.

These and other objects, features and advantages of the present invention will become readily apparent from the detailed description, which follows.

DETAILED DESCRIPTION OF THE PREFERRED EMBODIMENT

The present invention is directed towards a chemical composition and method of treatment utilizing the chemical composition which acts to absorb and bind undigested fat and rapidly eliminate the fat through the normal passage of waste from the human body prior to digestion or absorption of the fat. As a result of substantially reducing fat absorption, the present invention is also directed to a method of significantly reducing the production and cardio-vascular build-up of harmful cholesterol in humans.

In the preferred embodiment, the chemical composition of the present invention primarily comprises at least one fibrous agent to act both as a vehicle for absorbing fat and, through substantial reduction in fat absorption, as a medium for allowing a significant reduction in the production and/or collection of cholesterol in the human body. In the more preferred embodiment, a single fibrous agent is used, which ideally is psyllium and which comprises generally about 84% to 85% by weight of the composition. In the most preferred embodiment, however, psyllium comprises generally about 85% by weight of the composition. In alternative preferred embodiments, the chemical composition of the present invention may comprise one or more other fibrous agents in addition to psyllium. For example, plantago ovata seed mucilage or the cover or husks of psyllium seeds may be utilized, which are very fibrous materials. Other fibrous agents in addition to psyllium may also be utilized, as described more fully below.

In addition to the fibrous agent psyllium, the composition of the present invention preferably also comprises glucosamine, a material derived from deacetylated shellfish shells or chitin. Chitin is known in the art as a naturally occurring polysaccharide—a polymer of long molecules consisting of sugar molecules strung together as shown by the general formula:

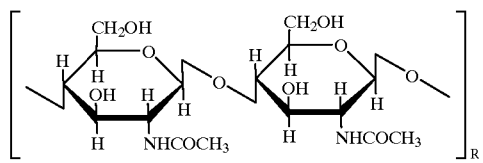

Chitin, which can be obtained from crab, lobster or shrimp shells by dissolving the shells' calcium carbonate and then removing protein fragments, leaving behind chitin as a white powder, normally cycles through the environment, decomposing naturally into it hydrogen, carbon, nitrogen and oxygen building blocks. In one embodiment of the invention, glucosamine may be obtained from chitin by hydrolysis. Preferably, glucosamine salts and compounds derived from a monomer of chitin, namely, N-acetyl-D-glucosamine (GlcN Ac) which is represented by the general formula:

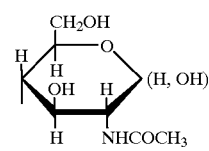

will be utilized such as, for example, glucosamine hydrochloride, acetylated glucosamines, and/or D-glucosamine. In a most preferred embodiment, glucosamine HCL and/or glucosamine hydrochloride will be utilized and will comprise generally about six (6%) percent to seven (7%) percent, and ideally, six (6%) percent by weight of the composition. Glucosamine hydrochloride offers an additional side benefit in that it has been shown to be an efficacious alternative to corticosteroid treatment of enteritis and colonitis. It will be understood by those of ordinary skill in the art that as a derivative of chitosan, which has an ability to chelate various metal ions because of its hydroxy and amino groups act as electron donors, glucosamine HCL is an ion, or molecule having a negative charge, and which therefore, attracts and binds with certain molecules of food. In an alternative embodiment, a betaalkylglycoside of N-acetyl-D-glucosamine may be utilized, which is represented by the general formula:

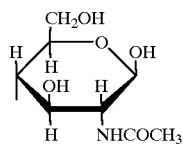

and is believed to effectively increase the ability of one's digestive tract to handle substantial quantities of lactose. In yet another alternative embodiment, the composition may comprise chitosan, instead of glucosamine. Chitosan is formed by adding the chitin, in its white power form, to a concentrated sodium hydroxide solution which has been heated to above 135 degrees Celsius. This serves to remove one of chitin's side groups, i.e., to hydrolize the N-acetyl linkage, resulting in chitosan, which can be more readily dissolved. Chitosan, which is represented by the general formula:

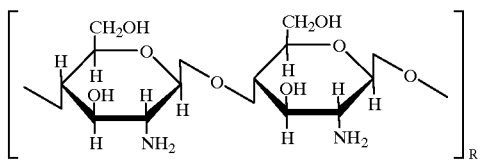

also has the ability to act as a coagulant, i.e., to attract and bind with certain molecules such as amino acids and proteins.

In the preferred embodiment of the present invention, the chemical composition comprises, in addition to psyllium and glucosamine HCL, a quantity of glucomannan—also known as Konjak or Konjac Root—which serves the purposes of providing lubrication and as well as providing an additional fibrous agent to the composition. Ideally, glucomannan comprises generally about five (5%) percent to six percent (6%), and ideally, six (6%) percent by weight of the composition. In addition, the chemical composition further comprises a pectin derived from fruits or succulent vegetables which serves the purpose of providing an additional fibrous agent to the composition. Most preferably, an apple pectin is used to form the composition which ideally, comprises generally about two percent (2%) by weight of the composition. Finally, in the preferred embodiment, the chemical composition also comprises a saturated fatty acid such as stearic acid, which serves the purpose of facilitating the processing and handling of a capsule containing the composition by permitting it to be smooth. Ideally, stearic acid comprises generally about one percent (1%) by weight of the composition.

In the preferred embodiment, the psyllium, glucosamine HCL, glucomannan, apple pectin and stearic acid are mixed together in powder form, although a granular form might also be suitable, and result in a mixture which is inert until it comes into contact with water, or other liquids such as is produced by the human body during digestion. Thus, in a most preferred embodiment, the present invention can be formed into capsules to facilitate ingestion, as well as packaging and storage. Additionally, the material used to form the encasement of the capsule will be inert when dry and upon coming into contact with water or other liquid will break down and permit both the release and subsequent activation of the chemical composition. Capsules also have the advantage of dissolving in a shorter period of time, thereby exposing the chemical composition to ingested fat in a shorter amount of time after ingestion. Single doses of the composition could be formed into pills which would require ingestion by humans at a longer period of time before meals are consumed. If desired, the capsules containing the chemical composition according to the present invention may be packaged into bottles or like containers having a capacity for 50, 60, 75, 80, 100 or more capsules. Such packaging containers may also include a small, separately wrapped quantity of drying agent, such as a silica gel, in order to assume a dry storage environment desirable for preserving the inertness of the composition until use.

Ideally, the preferred embodiment of the chemical composition of the present invention will be formed into capsules containing generally about seven hundred milligrams (700 mgs) of the chemical composition in the following amounts: generally about 85% by weight of psyllium; generally about 6% by weight of glucosamine HCL; generally about 6% by weight of glucomannan; generally about 2% by weight of apple pectin; and generally about 1% by weight of stearic acid. It will be appreciated that a capsule containing about 700 milligrams has a size and overall dimension which is readily suited for being comfortably swallowed by a person in quantities corresponding to recommended doses. However, the capsule could be formed to contain less or more of the chemical composition (with ratios of the composition similar to that disclosed therein), and thereby be somewhat larger or smaller, and still be adequate for ingestion by a person. Testing experiments with the above described chemical composition have demonstrated the ability of the chemical composition to absorb at least 5 times its own weight in fat. For instance, in one experiment 70 milliliters of water was placed in an appropriately sized test tube along with 10 grams (10,000 mg) of wheat germ oil and 100 milligrams of lecithin, the latter used as a substitute to replicate the emulsifying effect of gastric fluids normally present in a person's stomach. This mixture was shaken vigorously for about 10 seconds. Next, 1 gram (1000 mg) of the chemical composition according to the present invention was added and again, the mixture was shaken vigorously for about 10 seconds. After several minutes, the mixture was observed as having approximately fifty (50%) percent of fat (oil layer) gone, i.e., fat was no longer visible but instead had become bound with the fibrous agent of the composition so as to form an undigestible mass.

In addition to a reduction in cholesterol, the chemical composition of the present invention lends itself to a method of aiding human weight loss, which will now be described. In particular, the chemical composition of the present invention seeks out and binds with fat ingested by a human prior to its being absorbed into the body, and as has been explained, binds them to a fibrous agent so as to aid the person in feeling "full" and further, to permit rapid and natural elimination by the human body. The preferred method of the present invention comprises the steps of forming a capsule of generally about 700 milligrams with the chemical composition and having the human ingest at least four of the 700 milligram capsules with generally about eight ounces of water about fifteen to twenty minutes before a meal. Ideally however, the human will ingest four of the capsules before each meal. Thus, the intake of psyllium with each capsule is generally about six hundred milligrams (600 mgs) or multiplying by four, twenty-four hundred milligrams (2400 mgs) per meal, and if three meals a day are eaten, the intake would then be seventy-two hundred milligrams (7200 mgs) of psyllium per day, which amount has been shown to significantly aid with reducing cholesterol. From the foregoing, it should be clear that the human may ingest more than four such capsules, e.g., up to about six or more of the capsules if the meal to be eaten is especially large and/or has a particularly high fat content. Upon being ingested by a human, each capsule begins to disintegrate and releases or otherwise facilitates activation of the chemical composition contained therein in typically, generally about thirty (30) minutes, and often less time. In a preferred form of the method there is an additional step of having the human ingest generally about eight ounces of water upon waking upon in the morning, and ideally, there is an additional step of having the human ingest about eight ounces of water between meals.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed:

1. A chemical composition designed for the reduction of cholesterol in the human body, said composition comprising:
    a) an amount of psyllium in quantities generally between 84% and 85% by weight of said composition;
    b) an amount of glucosamine HCL generally between 6% and 7% by weight of said composition;
    c) an amount of glucomannan generally between 5% and 6% by weight of said composition, and
    d) an amount of fruit or vegetable derived pectin generally about 2% by weight of said composition.

2. A chemical composition as recited in claim 1 wherein said fruit or vegetable derived pectin is apple pectin.

3. A chemical composition as recited in claim 2 further comprising an amount of stearic acid generally between 1% and 2% by weight of said composition.

4. A chemical composition as recited in claim 1 further comprising an amount of stearic acid generally between 1% and 2% by weight of said composition.

5. A chemical composition as recited in claim 1 comprising a single dose of said composition defined by substantially seven hundred milligrams of said composition.

6. A chemical composition as recited in claim 5 wherein the single dose comprises a capsule.

7. A chemical composition for reducing cholesterol in the human body resulting from the ingestion of fatty foods, said composition comprising:
    a) an amount of psyllium generally about 85% by weight of said composition,
    b) an amount of glucosamine generally about 6% by weight of said composition,
    c) an amount of glucomannan generally about 6% by weight of said composition, and
    d) an amount of fruit or vegetable derived pectin generally about 2% by weight of said composition.

8. A chemical composition as recited in claim 7 wherein said fruit or vegetable derived pectin is apple pectin.

9. A chemical composition as recited in claim 8 further comprises an amount of stearic acid generally about 1% by weight of said composition.

10. A chemical composition for reducing cholesterol in the human body resulting from the ingestion of fatty foods, said composition comprising:
    a) an amount of psyllium in quantities generally between 84% and 85% by weight of said composition.
    b) an amount of chitosan generally between 6% and 7% by weight of said composition,
    c) an amount of glucomannan generally between 5% and 6% by weight of said composition, and
    d) an amount of apple pectin generally about 2% by weight of said composition.

11. A chemical composition as recited in claim 10 further comprising an amount of stearic acid generally between 1% and 2% by weight of said composition.

12. A method of reducing cholesterol in the human body, said method comprising the steps of:
    a) forming a single dose having a predetermined quantity of a chemical composition comprising:
        i) an amount of psyllium in quantities generally between 84% and 85% by weight of said composition,
        ii) an amount of glucosamine HCL generally between 6% and 7% by weight of said composition,
        iii) an amount of glucomannan generally between 5% and 6% by weight of said composition,
        iv) an amount of apple pectin generally about 2% by weight of said composition, and
    b) having a human ingest a predetermined quantity of said single dose prior to a meal.

13. A method as recited in claim 12 comprising forming the single dose by further including an amount of stearic acid generally between 1% and 2% by weight of said composition.

14. A method as recited in claim 11 comprising having the human ingest an amount of at least substantially 2800 milligrams of said composition.

15. A method as in claim 12 comprising defining the single dose to be an amount of substantially about 700 milligrams.

16. A method as in claim 15 comprising having a human ingest at least four doses of said composition before each meal.

17. A method as in claim 16 wherein said single dose is in capsule form.

18. A method of reducing cholesterol in the human body, said method comprising the steps of forming a single dose having a predetermined quantity of a chemical composition comprising:
    a) an amount of psyllium in quantities in generally about 85% by weight of said composition,
       an amount of chitosan generally about 6% by weight of said composition,
       an amount of glucomannan generally about 6% by weigh of said composition,
       an amount of apple pectin generally about 2% by weight of said composition,
    b) having a human ingest a predetermined quantity of said single dose prior to a meal.

19. A method as recited in claim 18 comprising having the human ingest an amount of at least 2800 milligrams of said composition prior to each meal.

20. A method as recited in claim 18 further comprising forming the single dose of said chemical composition into a capsule of substantially about 700 milligrams.

* * * * *